(12) United States Patent
Dragonuk et al.

(10) Patent No.: US 6,815,594 B2
(45) Date of Patent: Nov. 9, 2004

(54) INBRED CORN LINE G1202

(75) Inventors: Mike Dragonuk, Monticello, IL (US); Larry K. Boze, Monticello, IL (US)

(73) Assignee: Advanta Technology Ltd., Sleaford (GB)

(*) Notice: Subject to any disclaimer, the term of this patent is extended or adjusted under 35 U.S.C. 154(b) by 0 days.

(21) Appl. No.: 10/098,189

(22) Filed: Mar. 13, 2002

(65) Prior Publication Data

US 2003/0177546 A1 Sep. 18, 2003

(51) Int. Cl.[7] ............................ A01H 1/00; A01H 5/00; A01H 5/10; C12N 15/82
(52) U.S. Cl. .................. 800/320.1; 800/265; 800/275; 800/278; 800/279; 800/295; 435/412; 435/430; 435/430.1
(58) Field of Search ............................... 800/320.1, 265, 800/275, 279, 278, 295, 260, 300, 300.1, 301, 266, 267, 268, 276, 298; 435/412, 430, 430.1, 421, 424, 419, 468

(56) References Cited

U.S. PATENT DOCUMENTS 6,150,590 A * 11/2000 Arthur et al. ............ 800/320.1

FOREIGN PATENT DOCUMENTS

EP 0 160 390 3/1985

OTHER PUBLICATIONS

Conger, B.V., F.J. Novak, R. Afza, and K. Erdelsky. "Somatic embryogenesis from cultured leaf segments of Zea mays", Plant Cell Reports, 6:345–347 (1987).

Duncan, D.R., M.E. Williams, B.E. Zehr and J.M. Widholm. "The production of callus capable of plant regeneration from immature embryos of numerous Zea mays genotypes", Planta, 165:322–332 (1985).

Edallo, et al., "Chromosomal Variation and Frequency of Spontaneous Mutation Associated with in Vitro Culture and Plant Regeneration in Maize" Maydica XXVI, pp. 39–56 (1981).

Forsberg, R.A. and R.R. Smith. "Sources, Maintenance, and Utilization of Parental Material", Hybridization of Crop Plants, Chapter 4, pp. 65–81 (1980).

Green, C.E. and R.L. Phillips. "Plant Regeneration from Tissue Cultures of Maize", Crop Science, vol. 15, pp. 417–421 (1975).

Green, C.E. and C.A. Rhodes. "Plant Regeneration in Tissue Cultures of Maize", Maize for Biological Research, pp. 367–372 (1982).

Hallauer, et al, "Corn Breeding", Corn and Corn Improvement pp. 463–564 (1988). Sprague et al, eds.

Meghji, M.R., J.W. Dudley, R.J. Lambert, and G.F. Sprague. "Inbreeding Depression, Inbred and Hybrid Grain Yields, and Other Traits of Maize Genotypes Representing Three Eras". Crop Science, vol. 24, pp. 545–549 (1984).

Phillips, et al., "Cell/Tissue Culture and In Vitro Manupulation", In Corn & Corn Improvement, 3rd Ed., ASA Publication, #18, pp. 345–349 & 356–357 (1988).

Poehlman, John Milton. Breeding Field Crop, AVI Publishing Company, Inc., Westport, Connecticut, pp. 237–246 (1987).

Sass (1977) "Morphology". In Corn & Corn Improvement. ASA Publication. Madison, Wi, pp. 89–109.

Songstad, David D., David R. Duncan, and Jack M. Widholm. "Effect of 1–aminocyclopropane–1–carboxylic acid, silver nitrate, and norbornadiene on plant regeneration from maize callus cultures", Plant Cell Reports, 7:262–265 (1988).

M.P. Rolston. "Use of Endophyte in Plant Breeding and the Commercial Release of New Endophyte–Grass Associations". Proc. of the second Int'l Symposium on Acremonium/Grass Interactions: Plenary Papers (p. 171–174).

Tomes, et al, "the Effect of Parental Genotype on Initiation of Embryogenic Callus from Elite Maize (Zea mays 1.)Germplasm". Theor. Appl. Genet. 70., pp. 505–509. (1985).

Troyer, et al., "Selection for Early Flowering in Corn: 10 Late Synthetics". Crop Science, vol. 25, pp. 695–697 (1985).

Umbeck, et al. "Reversion of Male–Sterile T–Cytoplasm Maize to Male Fertility in Tissue Culture", Crop Science vol. 23, pp. 584–588 (1983).

Wright, H., "Commercial Hybrid Seed Production", Hybridization of Crop Plants, pp. 161–176 (1980).

Wych, R.D., "Production of Hybrid Seed Corn"; Corn and Corn Improvement, pp. 565–607 (1988).

* cited by examiner

Primary Examiner—Amy J. Nelson
Assistant Examiner—Medina A. Ibrahim
(74) Attorney, Agent, or Firm—Dana S. Rewaldt

(57) ABSTRACT

Broadly this invention provides an invention which is inbred corn line G1202. The methods for producing a corn plant by crossing the inbred line G1202 are also encompassed by the invention. Additionally, the invention relates to the various parts of inbred G1202 including culturable cells. This invention relates to hybrid corn seeds and plants produced by crossing the inbred line G1202 with at least one other corn line.

18 Claims, No Drawings

INBRED CORN LINE G1202

FIELD OF THE INVENTION

This invention is in the field of corn breeding, specifically relating to an inbred corn line designated G1202. This invention also is in the field of hybrid maize production employing the present inbred.

BACKGROUND OF THE INVENTION

The original maize plant was indigenous to the Western Hemisphere. The plants were weedlike and only through the efforts of early breeders were cultivated crop species developed. The crop cultivated by early breeders, like the crop today, could be wind pollinated. The physical traits of maize are such that wind pollination results in self-pollination or cross-pollination between plants. Each plant has a separate male and female flower that contributes to pollination, the tassel and ear, respectively. Natural pollination occurs when wind transfers pollen from tassel to the silks on the corn ears. This type of pollination has contributed to the wide variation of maize varieties present in the Western Hemisphere.

The development of a planned breeding program for maize only occurred in the last century. A large part of the development of the maize product into a profitable agricultural crop was due to the work done by land grant colleges. Originally, maize was an open pollinated variety having heterogeneous genotypes. The maize farmer selected uniform ears from the yield of these genotypes and preserved them for planting the next season. The result was a field of maize plants that were segregating for a variety of traits. This type of maize selection led to, at most, incremental increases in seed yield.

Large increases in seed yield were due to the work done by land grant colleges that resulted in the development of numerous hybrid corn varieties in planned breeding programs. Hybrids were developed by selecting corn lines and selfing these lines for several generations to develop homozygous pure inbred lines. One selected inbred line was crossed with another selected inbred line to produce hybrid progeny (F1). The resulting hybrids, due to heterosis, are robust and vigorous plants. Inbreds on the other hand are mostly homozygous. This homozygosity renders the inbred lines less vigorous. Inbred seed can be difficult to produce since the inbreeding process in corn lines decreases the vigor. However, when two inbred lines are crossed, the hybrid plant evidences greatly increased vigor and seed yield compared to open pollinated, segregating maize plants. An important consequence of the homozygosity and the homogenity of the inbred maize lines is that all hybrid seed produced from any cross of two such elite lines will be the same hybrid seed and make the same hybrid plant. Thus the use of inbreds makes hybrid seed which can be reproduced readily. The hybrid plant in contrast does not produce hybrid seed that is readily reproducible. The seed on a hybrid plant is segregating for traits.

The ultimate objective of the commercial maize seed companies is to produce high yielding, agronomically sound plants that perform well in certain regions or areas of the Corn Belt. To produce these types of hybrids, the companies must develop inbreds, which carry needed traits into the hybrid combination. Hybrids are not often uniformly adapted for the entire Corn Belt, but most often are specifically adapted for regions of the Corn Belt. Northern regions of the Corn Belt require shorter season hybrids than do southern regions of the Corn Belt. Hybrids that grow well in Colorado and Nebraska soils may not flourish in richer Illinois and Iowa soil. Thus, a variety of major agronomic traits are important in hybrid combination for the various Corn Belt regions, and have an impact on hybrid performance.

Inbred line development and hybrid testing have been emphasized in the past half-century in commercial maize production as a means to increase hybrid performance. Inbred development is usually done by pedigree selection. Pedigree selection can be selection in an $F_2$ population produced from a planned cross of two genotypes (often elite inbred lines), or selection of progeny of synthetic varieties, open pollinated, composite, or backcrossed populations. This type of selection is effective for highly inheritable traits, but other traits, for example, yield requires replicated test crosses at a variety of stages for accurate selection.

Maize breeders select for a variety of traits in inbreds that impact hybrid performance along with selecting for acceptable parental traits. Such traits include: yield potential in hybrid combination; dry down; maturity; grain moisture at harvest; greensnap; resistance to root lodging; resistance to stalk lodging; grain quality; disease and insect resistance; ear and plant height. Additionally, Hybrid performance will differ in different soil types such as low levels of organic matter, clay, sand, black, high pH, low pH; or in different environments such as wet environments, drought environments, and no tillage conditions. These traits appear to be governed by a complex genetic system that makes selection and breeding of an inbred line extremely difficult. Even if an inbred in hybrid combination has excellent yield (a desired characteristic), it may not be useful because it fails to have acceptable parental traits such as seed yield, seed size, pollen production, good silks, plant height, etc.

To illustrate the difficulty of breeding and developing inbred lines, the following example is given. Two inbreds compared for similarity of 29 traits differed significantly for 18 traits between the two lines. If 18 simply inherited single gene traits were polymorphic with gene frequencies of 0.5 in the parental lines, and assuming independent segregation (as would essentially be the case if each trait resided on a different chromosome arm), then the specific combination of these traits as embodied in an inbred would only be expected to become fixed at a rate of one in 262,144 possible homozygous genetic combinations. Selection of the specific inbred combination is also influenced by the specific selection environment on many of these 18 traits which makes the probability of obtaining this one inbred even more remote. In addition, most traits in the corn genome are regrettably not single dominant genes but are multi-genetic with additive gene action not dominant gene action. Thus, the general procedure of producing a non-segregating $F_1$ generation and self-pollinating to produce a $F_2$ generation that segregates for traits and selecting progeny with the visual traits desired does not easily lead to a useful inbred. Great care and breeder expertise must be used in selection of breeding material to continue to increase yield and the agronomics of inbreds and resultant commercial hybrids.

Certain regions of the Corn Belt have specific difficulties that other regions may not have. Thus the hybrids developed from the inbreds have to have traits that overcome or at least minimize these regional growing problems. Examples of these problems include in the eastern corn belt Gray Leaf Spot, in the north cool temperatures during seedling emergence, in the Nebraska region CLN (corn Lethal necrosis and in the west soil that has excessively high pH levels. The industry often targets inbreds that address these issues specifically forming niche products. However, the aim of most large seed producers is to provide a number of traits to each inbred so that the corresponding hybrid can useful in broader regions of the Corn Belt. The new biotechnology techniques such as Microsatellites, RFLPs, RAPDs and the like have provided breeders with additional tools to accomplish these goals.

SUMMARY OF THE INVENTION

The present invention relates to an inbred corn line G1202. Specifically, this invention relates to plants and seeds of this line. Additionally, this relates to a method of producing from this inbred, hybrid seed corn and hybrid plants with seeds from such hybrid seed. More particularly, this invention relates to the unique combination of traits that combine in corn line G1202.

Generally then, broadly the present invention includes an inbred corn seed designated G1202. This seed produces a corn plant.

The invention also includes the tissue culture of regenerable cells of G1202 wherein the cells of the tissue culture regenerates plants capable of expressing the genotype of G1202. The tissue culture is selected from the group consisting of leaves, pollen, embryos, roots, root tips, guard cells, ovule, seeds, anthers, silk, flowers, kernels, ears, cobs, husks and stalks, cells and protoplasts thereof. The corn plant regenerated from G1202 or any part thereof is included in the present invention. The present invention includes regenerated corn plants that are capable of expressing G1202's genotype, phenotype or mutants or variants thereof.

The invention extends to hybrid seed produced by planting, in pollinating proximity which includes using preserved maize pollen as explained in U.S. Pat. No. 5,596,838 to Greaves, seeds of corn inbred lines G1202 and another inbred line if preserved pollen is not used; cultivating corn plants resulting from said planting; preventing pollen production by the plants of one of the inbred lines if two are employed; allowing cross pollination to occur between said inbred lines; and harvesting seeds produced on plants of the selected inbred. The hybrid seed produced by hybrid combination of plants of inbred corn seed designated G1202 and plants of another inbred line are apart of the present invention. This inventions scope covers hybrid plants and the plant parts including the grain and pollen grown from this hybrid seed.

The invention further includes a method of hybrid F1 production. A first generation (F1) hybrid corn plant produced by the process of planting seeds of corn inbred line G1202; cultivating corn plants resulting from said planting; permitting pollen from another inbred line to cross pollinate inbred line G1202; harvesting seeds produced on plants of the inbred; and growing a harvested seed are part of the method of this invention.

Likewise included is a first generation (F1) hybrid corn plant produced by the process of planting seeds of corn inbred line G1202; cultivating corn plants resulting from said planting; permitting pollen from inbred line G1202 to cross pollinate another inbred line; harvesting seeds produced on plants of the inbred; and growing a plant from such a harvested seed.

The inbred corn line G1202 and at least one transgenic gene adapted to give G1202 additional and/or altered phenotypic traits are within the scope of the invention. Such transgenes are usually associated with regulatory elements (promoters, enhancers, terminators and the like). Presently, trangenes provide the invention with traits such as insect resistance, herbicide resistance, disease resistance increased or deceased starch or sugars or oils, increased or decreased life cycle or other altered trait.

The present invention includes inbred corn line G1202 and at least one transgenic gene adapted to give G1202 modified starch traits. Furthermore this invention includes the inbred corn line G1202 and at least one mutant gene adapted to give modified starch, acid or oil traits. The present invention includes the inbred corn line G1202 and at least one transgenic gene selected from the group consisting of: bacillus thuringiensis, the bar or pat gene encoding Phosphinothricin acetyl Transferase, Gdha gene, EPSP synthase gene, low phytic acid producing gene, and zein. The inbred corn line G1202 and at least one transgenic gene useful as a selectable marker or a screenable marker are covered by the present invention.

A tissue culture of the regenerable cells of hybrid plants produced with use of G1202 genetic material is covered by this invention. A tissue culture of the regenerable cells of the corn plant produced by the method described above are also included.

Definitions

In the description and examples, which follow, a number of terms are used. In order to provide a clear and consistent understanding of the specifications and claims, including the scope to be given such terms, the following definitions are provided.

Bl Moist

The moisture percentage of the grain at black layer, i.e., when 50% of the plants per plot have reached physiological maturity.

Cold Germ

Cold Germ is a measurement of seed germination under cold soil conditions. Data is reported as percent of seed germinating.

ECB

European corn borer is a maize eating insect. ECBI is the first brood generation of European corn borers. ECBII is the second generation of European corn borers. ECB1 is a rating of leaf damage. The ECBII (ECB2) rating is based upon tunneling. For all Entomology ratings, the higher number is best (1=little or no resistance, 9=highly resistant). The scale is slightly different for Ear Rating, which is taken on a 1–4 basis. This is a rating of corn borer feeding on the ear. A 1 represents feeding over the entire ear, while a 4 represents no observable feeding on the ear.

Emerge (EMG)

The number of emerged plants per plot (planted at the same seedling rate) collected when plants have two fully developed leaves.

GI

This is a selection index that provides a single quantitative measure of the worth of a hybrid based on four traits. FI is a very similar index which weights yield less than GI. In GI yield is the primary trait contributing to index values. The GI value is calculated by combining stalk lodging, root lodging, yield and dropped ears according to the attached mathematical formula:

$$GI=100+0.5(YLD)-0.9(\%\text{STALK LODGE})-0.9(\%\text{ROOT LODGE})-2.7(\%\text{DROPPED EAR})$$

GLS

Gray Leaf Spot (*Cercospora Zeae*) disease rating. This is rated on a 1–9 scale with a "1" being very susceptible, and a "9" being very resistant.*

GW
  Gross' Wilt (*Corynebacterium nebraskense*). This is rated on a 1–9 scale with a "1" being very susceptible, and a "9" being very resistant.*

HEATP10
  The number of Growing Degree Units (GDU's) or heat units required for an inbred line or hybrid to have approximately 10 percent of the plants shedding pollen. This trait is measured from the time of planting. Growing Degree Units are calculated by the Barger Method where the GDU's for a 24 hour period are:

$$GDU = \frac{(\text{Max Temp (° F.)} + \text{Min Temp (° F.)})}{2} - 50$$

The highest maximum temperature used is 86° F. and the lowest minimum temperature used is 50° F. For each inbred or hybrid it takes a certain number of GDU's to reach various stages of plant development.

HEATBL
  The number of GDU's after planting when approximately 50 percent of the inbred or hybrid plants in a plot have grain that has reached physiological maturity (black layer).

Heatpeek
  The number of GDU's after planting of an inbred when approximately 50 percent of the plants show visible tassel extension.

HEATP50 or HTP50
  The number of GDU's required for an inbred or hybrid to have approximately 50 percent of the plants shedding pollen. Growing Degree Units are calculated by the Barger Method as shown in the HEATP10 definition.

HEATP90
  The number of GDU's accumulated from planting when the last 100 percent of plants in an inbred or hybrid are still shedding enough viable pollen for pollination to occur. Growing Degree Units are calculated by the Barger Method as shown in the HEATP10 definition.

HEATS10
  The number of GDU's required for an inbred or hybrid to have approximately 10 percent of the plants with silk emergence of at least 0.5 inches. Growing Degree Units are calculated by the Barger Method as shown in the HEATP10 definition.

HEATS50 or HTS50
  The number of GDU's required for an inbred or hybrid to have approximately 50 percent of the plants with silk emergence of at least 0.5 inches. Growing Degree Units are calculated by the Barger Method as shown in the HEATP10 definition.

HEATS90
  The number of GDU's required for an inbred or hybrid to have approximately 90 percent of the plants with silk emergence of at least 0.5 inches. Growing Degree Units are calculated by the Barger Method as shown in the HEATP10 definition.

$MDMV_A$
  Maize Dwarf Mosaic Virus strain A. The corn is rated on a 1–9 scale with a "1" being very susceptible, and a "9" being very resistant.*

$MDMV_B$
  Maize Dwarf Mosaic Virus strain B. This is rated on a 1–9 scale with a "1" being very susceptible and a "9" being very resistant.*

Moisture
  The average percentage grain moisture of an inbred or hybrid at harvest time.

NLB
  Northern Leaf Blight (*Exserohilum turcicum*) disease rating. This is rated on a 1–9 scale with a "1" being very susceptible, and a "9" being very resistant.*

PCT Tiller or Tiller Rating
  The total number of tillers per plot divided by the total number of plants per plot.

Plant
  This term includes plant cells, plant protoplasts, plant cell tissue cultures from which corn plants can be regenerated, plant calli, plant clumps, and plant cells that are intact in plants or parts of plants, such as embryos, pollen, flowers, kernels, ears, cobs, leaves, husks, stalks, roots, root tips, anthers, silk and the like., and this term also includes any transgenic DNA or (RNA) or portion thereof that have been introduced into the plant by whatever method.

Plant Height (PLTHT) (PHT)
  The distance in centimeters from ground level to the base of the tassel peduncle.

Plant Integrity (PLTINT) or (INT)
  The level of plant integrity on a scale of 1–9 with 9 evidencing the trait most strongly: 1–2.9 ratings are low plant integrity, 3–5.9 ratings are intermediate plant integrity, and 6–9 ratings are strongly evidencing plant integrity.

Population (POP)
  The plant population.

RM
  Predicted relative maturity based on the moisture percentage of the grain at harvest. This rating is based on known set of checks and utilizes standard linear regression analyses and is referred to as the Minnesota Relative Maturity Rating System.

Shed
  The volume of pollen shed by the male flower rated on a 1–5 scale where a "1" is a very light pollen shedder, a "2.5" is a moderate shedder, and a "5" is a very heavy shedder.

SLB
  Southern Leaf Blight (*Bipolaris mavdis*) disease rating. This is rated on a 1–9 scale with a "1" being very susceptible, and a "9" being very resistant.*

Staygreen (SGN)
  The level of staygreen of the plant on a scale of 1–9 with 9 evidencing the trait most strongly: 1–2.9 ratings are low staygreen, 3–5.9 ratings are intermediate staygreen, and 6–9 ratings are strongly evidencing staygreen.

TWT
  The measure of the weight of grain in pounds for a one bushel volume adjusted for percent grain moisture.

Vigor (VIG)
  Visual rating of 1 to 9 made 2–3 weeks post-emergence where a "1" indicates very poor early plant development, and a "9" indicates superior plant development.

Warm Germ
  A measurement of seed germination under ideal (warm, moist) conditions. Data is reported as percent of seeds germinating.

Yield (YLD)
  Actual yield of grain at harvest adjusted to 15.5% moisture. Measurements are reported in bushels per acre.

% Dropped Ears (DE)

The number of plants per plot, which dropped their primary ear, divided by the total number of plants per plot.

% Root Lodge (RL)

Percentage of plants per plot leaning more that 30 degrees from vertical divided by total plants per plot.

% Stalk Lodge (SL)

Percentage of plants per plot with the stalk broken below the primary ear node divided by the total plants per plot.

Resistant—on a scale of 1–9 with 9 evidencing the trait most strongly: 1–2.9 ratings are susceptible, 3–5.9 ratings are intermediate, and 6–9 ratings are resistant.

DETAILED DESCRIPTION OF THE INVENTION

G1202 can be used as a male or female line. This inbred has an extended pollen shed across 235 heat units. The inbred has good levels of moisture at harvest and slightly low yields. In hybrid combination this line yields 115 day hybrids. The inbred carries tolerance to Gray Leaf Spot and Gross' Wilt.

The inbred has shown uniformity and stability within the limits of environmental influence for all the traits as described in the Variety Description Information (Table 1) that follows.

The inbred has been self-pollinated for a sufficient number of generations to give inbred uniformity. During plant selection in each generation, the uniformity of plant type was selected to ensure homozygosity and phenotypic stability. The line has been increased in isolated farmland environments with data on uniformity and agronomic traits being observed to assure uniformity and stability. No variant traits have been observed or are expected in G1202.

The best method of producing the invention, G1202 which is substantially homozygous, is by planting the seed of G1202 which is substantially homozygous and self-pollinating or sib pollinating the resultant plant in an isolated environment, and harvesting the resultant seed.

TABLE I

G1202
VARIETY DESCRIPTION INFORMATION

1 Type: Dent
2 Region Best Adapted: Broadly adapted - Central, Eastern regions of the Corn Belt. This inbred in hybrid combination has RM of 113–115.
3 Plant Traits

| | |
|---|---|
| Plant Height | 73 in. |
| Ear Height | 32 in. |
| Tillers (Rating) | 5 |
| Leaf Color | MEDIUM GREEN |
| Brace Root Color | GREEN |
| Silk Color | RED/PINK |
| Shoots at Flowering | BALD |

TABLE I-continued

G1202
VARIETY DESCRIPTION INFORMATION

4 Tassel Traits

| | |
|---|---|
| Glume Color | GREEN |
| Glume Ring Color | OTHER/ABSENT |
| Anther Color | YELLOW |

5 Ear and Kernel Traits

| | |
|---|---|
| Cob Color | RED |
| Kernel Crown Color | YELLOW |

6 Disease Resistance In Inbred

Gray Leaf Spot = 5.7
Gross' Wilt = 6.3

7 Insect Resistance In Inbred

ECB1 = 5.5
ECB2 = 4.27620
Ear rate = 2.3750

The comparable inbred to G1202 is ZS01101, an inbred having a number of similarities. ZS01101 is an inbred which has been or presently in commercial hybrids that are in similar region of adaptation as most of the hybrids formed with G1202.

The Munsell code is a reference book of color, which is known and used in the industry and by persons with ordinary skill in the art of plant breeding.

The purity and homozygosity of inbred G1202 is constantly being tracked using isozyme genotypes as shown in Table 2.

Isozyme Genotypes for G1202

Isozyme data were generated for inbred corn line G1202 according to procedures known and published in the art. The data in Table 2 gives the electrophoresis data on G1202 as compared to its two parents.

TABLE 2

ELECTROPHORESIS RESULTS FOR G1202

| INBRED | ACP1 | ACP4 | ADH | MDH1 | MDH2 | PGD1 | PGD2 | PHI | PGM | IDH |
|---|---|---|---|---|---|---|---|---|---|---|
| G1202 | 11 | 0 | 22 | 22 | 22 | 11 | 11 | 22 | 22 | 11 |

Inbred and Hybrid Performance of G1202

The traits and characteristics of inbred corn line G1202 are listed to compare with other inbreds and/or in hybrid combinations. The G1202 data shows the characteristics and traits of importance, giving a snapshot of G1202 in these specific environments.

Table 3A shows a comparison between G1202 and a comparable inbred ZS01101. G1202 has better vigor than does inbred ZS01101. The two inbreds show significant differences in ear height, plant height, and across all Heat measurements for pollination and silking. G1202 has significantly lower yield at harvest than does ZS01101 but has slightly lower moisture that is not significantly different. G1202 flowers significantly later than ZS0110lacross all pollination and silking data. G1202 reaches heat peak with significantly more heat units than does ZS01101. The present invention is slightly more full season than is ZS01101.

TABLE 3A

PAIRED INBRED COMPARISON DATA

| YEAR | INBRED | YIELD | MOISTURE | EAR HEIGHT | PLANT HEIGHT | EMERGE | HEAT PEEK | HEATP10 | HEATP50 |
|---|---|---|---|---|---|---|---|---|---|
| OVERALL | G1202 | 60.7 | 11.4 | 82.2 | 192.7 | 61.5 | 1425.2 | 1467.5 | 1513.7 |
|  | ZS01101 | 81.7 | 11.9 | 71.3 | 171.4 | 87.7 | 1355.5 | 1415.4 | 1452.1 |
|  | # EXPTS | 15 | 15 | 11 | 11 | 15 | 14 | 14 | 14 |
|  | DIFF | 20.9 | 0.5 | 10.9 | 21.3 | 26.2 | 69.7 | 52.1 | 61.6 |
|  | PROB | 0.032** | 0.319 | 0.026** | 0.001*** | 0.000*** | 0.000*** | 0.001*** | 0.001*** |

| YEAR | INBRED | HEATP90 | HEATS10 | HEATS50 | HEATS90 | % LRG MED FLAT | % LRG MED RND | % LRG PLATELESS |
|---|---|---|---|---|---|---|---|---|
| OVERALL | G1202 | 1702.3 | 1509.4 | 1561.6 | 1605.4 | 18.1 | 48.2 | 8.2 |
|  | ZS01101 | 1609 | 1422 | 1455.5 | 1501 | 10.7 | 12.5 | 0.4 |
|  | # EXPTS | 11 | 14 | 14 | 11 | 14 | 14 | 14 |
|  | DIFF | 93.4 | 87.5 | 106 | 104.4 | 7.5 | 35.8 | 7.8 |
|  | PROB | 0.001*** | 0.000*** | 0.000*** | 0.002*** | 0.003*** | 0.000*** | 0.000*** |

| YEAR | INBRED | % SML MED FLAT | % SML MED RND | % SML PLATELESS | % CULL | SHED | COLD GERM | WARM GERM |
|---|---|---|---|---|---|---|---|---|
| OVERALL | G1202 | 2.8 | 19.1 | 2.4 | 1 | 3.7 | 81.2 | 91.8 |
|  | ZS01101 | 22.2 | 26.9 | 21.2 | 6 | 4.1 | 92.9 | 97.4 |
|  | # EXPTS | 14 | 14 | 14 | 14 | 12 | 12 | 12 |
|  | DIFF | 19.5 | 7.9 | 18.7 | 4.9 | 0.4 | 11.7 | 5.6 |
|  | PROB | 0.000*** | 0.017** | 0.000*** | 0.009*** | 0.137 | 0.002*** | 0.000*** |

*.05 < PROB <= .10
**.01 < PROB <= .05
***.00 < PROD <= .01

TABLE 3B

PAIRED HYBRID COMPARISON DATA

| YEAR | HYBRID | % ROOT LODGE | % STALK LODGE | % DROPPED EARS | TEST WEIGHT | MOISTURE | YIELD | GI | Y_M | FI |
|---|---|---|---|---|---|---|---|---|---|---|
| OVERALL | CI/G1202 | 0.6 | 3.1 | 0 | 55.4 | 19.2 | 185.7 | 189.4 | 10.1 | 145.4 |
|  | 8342GLS/IT | 0.4 | 2.5 | 0 | 55.1 | 19.2 | 172 | 183.3 | 9.3 | 139.2 |
|  | # EXPTS | 294 | 294 | 293 | 290 | 296 | 296 | 293 | 296 | 293 |
|  | DIFF | 0.2 | 0.6 | 0 | 0.3 | 0 | 13.7 | 6 | 0.8 | 6.1 |
|  | PROB | 0.253 | 0.019** | 0.176 | 0.001*** | 0.88 | 0.000*** | 0.000*** | 0.000*** | 0.000*** |

*.05 < PROB <= .10
**.01 < PROB <= .05
***.00 < PROB <= .01

Table 3B shows the Inbred G1202 in hybrid combination with a common inbred and another hybrid combination that includes the same common inbred and another inbred. The comparison hybrid carries the IT (imazethapyr tolerance trait) and an increased level of grey leaf tolerance. When in these hybrid combinations the present inbred carries a slightly significant heavier test weight and a distinctively significant increase in yield into the hybrid. The Y/M for the hybrid combination containing the present invention is significantly higher than is the comparison hybrid's Y/M rating.

Table 4 shows the GCA (general combining ability) estimates of G1202 compared with the GCA estimates of the other inbreds. The estimates show the general combining ability is weighted by the number of experiment/location combinations in which the specific hybrid combination occurs. The interpretation of the data for all traits is that a positive comparison is a practical advantage. A negative comparison is a practical disadvantage. The general combining ability of an inbred is clearly evidenced by the results of the general combining ability estimates. This data compares the inbred parent in a number of hybrid combinations to a group of "checks". The check data is from other companies' hybrids, particularly the leader in the industry and Garst Seed's commercial products and pre-commercial hybrids, which were grown in the same sets and locations.

TABLE 4

|  | N | FI | Y/M | GI | YLD | MST | % SL | % RL | % DE | TWT | POP | RM |
|---|---|---|---|---|---|---|---|---|---|---|---|---|
|  |  |  |  |  | G1202 |  |  |  |  |  |  |  |
| XT = | 22 | 5.0 | 0.6 | 4.8 | 8.2 | 0.1 | 0.4 | 0.5 | 0.0 | 0.2 | −128 | 113 |
|  |  |  |  |  | ZS01101 |  |  |  |  |  |  |  |
| XT = | 9 | −0.3 | −0.0 | −0.7 | −1.7 | 0.2 | −0.2 | 0.6 | 0.0 | −0.1 | 129 | 112 |

FI = 100 + 0.5 (Yld) − 2.3 (MST) − 0.9 (% SL) − 0.9 (% RL) − 2.7 (% DE)
POP = plants per acre
RM = The Minnesota Relative Maturity
XT = GCA Estimate weighted by parent 2, but using only those parent 2 with two years of data Table 4 shows G1202 in XT crossed to different inbreds to form hybrid combinations.

G1202 in hybrid combination shows an excellent advantage for yield (YLD) and an advantage for yield/moisture (Y/M) compared to the commercial checks and the company's hybrids made with this inbred. When compared to ZS01101 G1202 has a slightly more positive rating for most of the agronomic traits except for resistance to root lodging. In a number of categories the present invention surpasses the ZS01101 line.

TABLE 5A

YIELD RESPONSE
Research Plots

| HYBRID |  |  | YIELD |  |  |  |
|---|---|---|---|---|---|---|
| G1202/Inbred X | 75 | 102 | 129 | 156 | 183 | 210 |
| Environment | 75 | 100 | 125 | 150 | 175 | 200 |

Error: 15.2
Plots 319

TABLE 5B

YIELD RESPONSE
Research Plots

| HYBRID |  |  | YIELD |  |  |  |
|---|---|---|---|---|---|---|
| ZS01101/Inbred X | 89 | 110 | 132 | 154 | 175 | 197 |
| Environment | 75 | 100 | 125 | 150 | 175 | 200 |

Error: 13.7
Plots 8173

Table 5A shows the yield response of G1202 in hybrid combination in comparison with the plants in the environment around it at the same location. The data for the present inbred is showing consistently better results than the data of the comparison hybrid until the highest environment level. G1202 in hybrid combination, is an inbred that works well by providing yields better than the environment in low-medium to high yielding environments. The yield is about equal to yields in the low yielding environments. Its performance shows that this is a consistent yielding inbred regardless of the environment. Table 5b shows the data from a different hybrid that was formed with the same common inbred as in the Table 5A. This comparison hybrid is still yielding well particularly in the low and middle environments but it is not carrying the yield potential into high yielding environments.

TABLE 6

DISEASE RESISTANCE IN BOTH INBREDS

G1202 shows the following disease resistance in the inbred:
Gray Leaf Spot = 5.7
Gross' Wilt = 6.3
In contrast ZS01101 shows the following disease resistance:
Gray Leaf Spot = 6.0
Gross' Wilt = 6.4

Thus the inbred G1202 carries similar levels of resistances to disease as does ZS01101. In many hybrid combinations the inbred G1202 carries these resistances to disease into the hybrid combination.

The foregoing is set forth by way of example and is not intended to limit the scope of the invention.

This invention also is directed to methods for producing a corn plant by crossing a first parent corn plant with a second parent corn plant wherein the first or second parent corn plant is an inbred corn plant from the line G1202. Further, both first and second parent corn plants can come from the inbred corn line G1202. A variety of breeding methods can be selected depending on the mode of reproduction, the trait, and the condition of the germplasm. Thus, any such methods using the inbred corn line G1202 are part of this invention: selfing, backcrosses, hybrid production, crosses to populations, haploid by such old and known methods of using stock material that induces haploids and anther culturing and the like. Additionally, this maize can, within the scope of the invention, contain: a mutant gene such as but not limited to sugary 1 or shrunken 1 or waxy or AE or imazethapyr tolerant (IT or IR™) mutant gene; or transgenic genes such as but not limited to insect resistant genes such as Bacillus thuringiensis (Cry genes), or herbicide resistant genes such as Pat gene or Bar gene, EPSP, or disease resistant genes such as the Mosaic virus resistant gene, etc., or trait altering genes such as flowering genes, oil modifying genes, senescence genes and the like.

Various culturing techniques known to those skilled in the art, such as haploid, (stock six is a method that has been in use for twenty years and is well known to those with skill in the art), transformation, and a host of other conventional and unconventional methods are within the scope of the invention. All plants and plant cells produced using the inbred corn line are within the scope of this invention. The term transgenic plant refers to plants having genetic sequences, which are introduced into the genome of a plant by a transformation method and the progeny thereof. Transformation methods are means for integrating new genetic coding sequences into the plant's genome by the incorporation of these sequences into a plant through man's assistance, but not by breeding practices.

Though there are a large number of known methods to transform plants, certain types of plants are more amenable to transformation than are others. Tobacco is a readily transformable plant. The basic steps of transforming plants including monocots are known in the art. These steps are concisely outlined in U.S. Pat. No. 5,484,956 "Fertile Transgenic Zea mays Plants Comprising Heterologous DNA Encoding Bacillus thuringiensis Endotoxin" issued Jan. 16, 1996 and U.S. Pat. No. 5,489,520 "Process of Producing Fertile Zea mays Plants and Progeny Comprising a Gene Encoding Phosphinothricin Acetyl Transferase" issued Feb. 6, 1996.

Plant cells such as maize can be transformed by a number of different techniques. Some of these techniques which have been reported on and are known in the art include maize pollen transformation (See University of Toledo 1993 U.S. Pat. No. 5,177,010); Biolistic gun technology (See U.S. Pat. No. 5,484,956); Whiskers technology (See U.S. Pat. Nos. 5,464,765 and 5,302,523); Electroporation; PEG on Maize; Agrobacterium (See 1996 article on transformation of maize cells in Nature Biotechnology, Volume 14, June 1996) along with numerous other methods which may have slightly lower efficiency rates. Some of these methods require specific types of cells and other methods can be practiced on any number of cell types.

The use of pollen, cotyledons, meristems and ovum as the target issue can eliminate the need for extensive tissue culture work. Generally, cells derived from meristematic tissue are useful. Zygotic embryos can also be used. Additionally, the method of transformation of meristematic cells of cereal is also taught in the PCT application WO96/04392. Any of the various cell lines, tissues, plants and plant parts can and have been transformed by those having knowledge in the art. Methods of preparing callus or protoplasts from various plants are well known in the art and specific methods are detailed in patents and references used by those skilled in the art. Cultures can be initiated from most of the above-identified tissue. The only true requirement of the transforming material is that it can form a transformed plant. The transgenic gene can come from various non-plant genes (such as; bacteria, yeast, animals, and viruses) along with being from plants.

The DNA used for transformation of these plants clearly may be circular, linear, and double or single stranded. Usually, the DNA is in the form of a plasmid. The plasmid usually contains regulatory and/or targeting sequences which assists the expression of the gene in the plant. The methods of forming plasmids for transformation are known in the art. Plasmid components can include such items as: leader sequences, transit polypeptides, promoters, terminators, genes, introns, marker genes, etc. The structures of the gene orientations can be sense, antisense, partial antisense, or partial sense: multiple gene copies can be used.

The regulatory promoters employed can be constitutive such as CaMv35S (usually for dicots) and polyubiquitin for monocots or tissue specific promoters such as CAB promoters, etc. The prior art includes but is not limited to octopine synthase, nopaline synthase, CaMv19S, mannopine synthase promoters. These regulatory sequences can be combined with introns, terminators, enhancers, leader sequences and the like in the material used for transformation.

The isolated DNA is then transformed into the plant. Many dicots can easily be transformed with Agrobacterium. Some monocots are more difficult to transform. As previously noted, there are a number of useful transformation processes. The improvements in transformation technology are beginning to eliminate the need to regenerate plants from cells. Since 1986, the transformation of pollen has been published and recently the transformation of plant meristems has been published. The transformation of ovum, pollen, and seedlings meristem greatly reduce the difficulties associated with cell regeneration of different plants or genotypes which a maize plant can present. Duncan, from at least 1985 produced literature on plant regeneration from callus. Both inbred and hybrid callus have resulted in regenerated plants. Somatic embryogenesis has been performed on various maize tissues, which was once considered unusable for this purpose. The prior art clearly teaches the regeneration of plants from various maize tissues.

The most common method of maize transformation is referred to as gunning or microprojectile bombardment though the other methods can be used. The Biolistic process has small gold-coated particles coated with DNA shot into the transformable material. Techniques for gunning DNA into cells, tissue, callus, embryos, and the like are well known in the prior art.

After the transformation of the plant material is complete, the next step is identifying the cells or material, which has been transformed. In some cases, a screenable marker is employed such as the beta-glucuronidase gene of the uidA locus of E. coli. Then, the transformed cells expressing the colored protein are selected for either regeneration or further use. In many cases, a selectable marker identifies the transformed material. The putatively transformed material is exposed to a toxic agent at varying concentrations. The cells not transformed with the selectable marker, which provides resistance to this toxic agent, die. Cells or tissues containing the resistant selectable marker generally proliferate. It has been noted that although selectable markers protect the cells from some of the toxic affects of the herbicide or antibiotic, the cells may still be slightly affected by the toxic agent by having slower growth rates. If the transformed material was cell lines then these lines are regenerated into plants. The cells' lines are treated to induce tissue differentiation. Methods of regeneration of cellular maize material are well known in the art.

All plants and plant cells produced using inbred corn line G1202 are within the scope of this invention. The invention encompasses the inbred corn line used in crosses with other, different, corn inbreds to produce (F1) corn hybrid seeds and hybrid plants. This invention includes cells, which upon growth and differentiation produce corn plants having the physiological and morphological characteristics of the inbred line G1202.

A deposit of at least 2500 seeds of this invention will be maintained by Advanta USA, Inc., 2369 330th Street, Slater, Iowa 50244. Access to this deposit will be available during the pendency of this application to the Commissioner of Patents and Trademarks and persons determined by the Commissioner to be entitled thereto upon request. All restrictions on availability to the public of such material will be removed upon issuance of a granted patent of this application by depositing at least 2500 seeds of this invention at the American Type Culture Collection (ATCC), at 10801 University Boulevard, Manassas, Va. 20110. The date of deposit was May 17, 2004 and the seeds were tested and found to be viable on May 24, 2004. The ATCC accession number is PTA-5972. The ATCC deposit will be maintained in that depository, which is a public depository, for a period of 30 years, or 5 years after the last request, or for the effective life of the patent, whichever is longer, and will be replaced if it becomes nonviable during that period.

Additional public information on some ZS designations may be available from the PVP Office, a division of the US Government.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. Inbred corn seed of the line designated G1202, wherein representative seed of said line have been deposited in the ATCC under Accession No. 5972.

2. A corn plant produced by growing the seed of claim 1.

3. A tissue culture of regenerable cells produced from the corn plant of claim 2.

4. The tissue culture according to claim 3, wherein the regenerable cells are from a tissue selected from the group consisting of: leaf, pollen, embryo, root, root tip, meristem, ovule, anther, silk, flower, kernel, ear, cob, husk and stalk.

5. A corn plant regenerated from the tissue culture of claim 3, wherein the regenerated plant has all of the physiological and morphological characteristics of a corn plant of the inbred line designated G1202, wherein representative seed of said inbred line have been deposited in the ATCC under accession number X.

6. A method of introducing a desired trait into corn inbred line G1202 comprising:
   (a) crossing G1202 plants grown from seed deposited under ATCC Accession No. 5972, with plants of another corn line that comprise a desired trait to produce FI progeny plants, wherein the desired trait is selected from, male sterility, herbicide resistance, insect resistance, and resistance to disease;
   (b) selecting FI progeny plants that have the desired trait to produce selected FI progeny plants;
   (c) crossing the selected progeny plants with inbred G1202 plants to produce backcross progeny plants;
   (d) selecting for backcross progeny plants that have the desired trait and physiological and morphological characteristics of corn inbred plant G1202 to produce selected backcross progeny plants; and
   (e) repeating steps (c) and (d) three or more times in succession to produce selected fourth or higher backcross progeny plants that comprise the desired trait and all of the physiological and morphological characteristics of corn inbred line G1202 listed in Table 1 as determined at the 5% significance level when grown in the same environmental conditions.

7. Pollen of the corn plant of claim 2.

8. A corn plant produced by the method of claim 6, wherein the plant has the desired trait and all of the physiological and morphological characteristics of corn inbred line G1202 listed in Table 1 as determined at the 5% significance level when grown in the same environmental conditions.

9. A method for producing an F1 hybrid corn seed, comprising crossing the plant of claim 2, with a different corn plant and harvesting the resultant F1 hybrid corn seed.

10. A method for producing an herbicide resistant corn plant comprising transforming the corn plant of claim 2, with a transgene that confers herbicide resistance.

11. An herbicide resistant corn plant produced by the method of claim 10.

12. The corn plant of claim 11, wherein the transgene confers resistance to an herbicide selected from the group consisting of: imidazolinone, glyphosate, glufosinate, and phosphinothricin.

13. A method of producing an insect resistant corn plant comprising transforming the corn plant of claim 2 with a transgene that confers insect resistance.

14. An insect resistant corn plant produced by the method of claim 13.

15. The corn plant of claim 14, wherein the transgene encodes a *Bacillus thuringiensis* endotoxin.

16. A method of producing a disease resistant corn plant comprising transforming the corn plant of claim 2 with a transgene that confers disease resistance.

17. A disease resistant corn plant produced by the method of claim 16.

18. Seed produced by selfing the plant according to claim 2, wherein said seed produce plants having all the physiological and morphological characteristics of a corn plant of the inbred line G1202, seed of said inbred line having been deposited under ATCC Accession No: 5972.

* * * * *